(12) United States Patent
Hung et al.

(10) Patent No.: US 10,456,025 B2
(45) Date of Patent: Oct. 29, 2019

(54) TRACHEAL INTUBATION DEVICE

(71) Applicants: Orlando Ricardo Hung, Halifax (CA); Andrew Davidson Milne, Halifax (CA); Matthew Ivan d'Entremont, Lakeview (CA)

(72) Inventors: Orlando Ricardo Hung, Halifax (CA); Andrew Davidson Milne, Halifax (CA); Matthew Ivan d'Entremont, Lakeview (CA)

(73) Assignee: SCOTIA M.D. ENGINEERING INC., Halifax, Nova Scotia (CA)

( * ) Notice: Subject to any disclaimer, the term of this patent is extended or adjusted under 35 U.S.C. 154(b) by 719 days.

(21) Appl. No.: 14/309,970

(22) Filed: Jun. 20, 2014

(65) Prior Publication Data

US 2015/0297071 A1     Oct. 22, 2015

(30) Foreign Application Priority Data

Apr. 17, 2014  (CA) ...................................... 2849580

(51) Int. Cl.
*A61B 1/267* (2006.01)
*A61M 16/04* (2006.01)

(52) U.S. Cl.
CPC .................................. *A61B 1/267* (2013.01)

(58) Field of Classification Search
CPC .............. A61M 16/00; A61M 16/0084; A61M 16/04–053; A61M 16/0436; A61M 16/0467; A61M 16/0488; A61M 16/06–0655; A61M 25/02; A61M 39/00; A61B 1/00; A61B 1/00043–00052;
(Continued)

(56) References Cited

U.S. PATENT DOCUMENTS 3,983,996 A * 10/1976 Hendren, III ....... A61M 25/002
206/363
5,030,227 A * 7/1991 Rosenbluth ........ A61M 25/1011
600/116
(Continued)

OTHER PUBLICATIONS

Yamamura et al. "M. K. Device for Blind Nasal Intubation", Anesthesiology, vol. 20, p. 221 (1959).

*Primary Examiner* — Tan-Uyen T Ho
*Assistant Examiner* — Ned T Heffner
(74) *Attorney, Agent, or Firm* — Thompson Hine LLP

(57) ABSTRACT

An intubation device for placing a tracheal tube into a patient's trachea. The intubation device comprises a flexible light-wand having light emitting means placed in a distal end portion thereof. A distal portion of the flexible light-wand is adapted for placement inside the tracheal tube with the distal end portion thereof being in proximity to a distal end of the tracheal tube. The intubation device further comprises a coupling conduit. The coupling conduit has a tracheal tube port for being connected to the tracheal tube placed at a distal end thereof, a ventilating port for being connected to a ventilatory source, a monitoring port for being connected to a respiratory gas monitor, and a sealed aperture placed at a proximal end thereof. The sealed aperture accommodates the flexible light wand therethrough in a sealed fashion such that ventilating and monitoring of the patient is enabled while the flexible light wand is placed in the tracheal tube.

14 Claims, 16 Drawing Sheets

(58) Field of Classification Search
CPC ...... A61B 1/00188–00197; A61B 1/24; A61B 1/267–2676; A61B 5/0033
See application file for complete search history.

(56) References Cited

U.S. PATENT DOCUMENTS

| | | | |
|---|---|---|---|
| 5,158,569 A * | 10/1992 | Strickland | A61M 16/0463 128/202.16 |
| 5,163,841 A | 11/1992 | Schreinemakers | |
| 5,163,941 A | 11/1992 | Garth et al. | |
| 5,337,735 A | 8/1994 | Salerno | |
| 5,394,865 A | 3/1995 | Salerno | |
| 5,672,179 A | 9/1997 | Garth et al. | |
| 6,068,644 A * | 5/2000 | Lulo | A61B 17/12022 606/191 |
| 6,860,264 B2 | 3/2005 | Christopher | |
| 7,052,456 B2 | 5/2006 | Simon | |
| 8,677,990 B2 | 3/2014 | Gabriel | |
| 8,746,239 B2 | 6/2014 | Yoshida | |
| 8,894,569 B2 | 11/2014 | Qiu | |
| 2006/0157059 A1 | 7/2006 | Johnson et al. | |
| 2007/0129603 A1 | 6/2007 | Hirsh | |
| 2008/0017195 A1* | 1/2008 | Yoshida | A61M 16/0488 128/200.26 |
| 2009/0050146 A1 | 2/2009 | Smith | |
| 2013/0041227 A1 | 2/2013 | Chan et al. | |

* cited by examiner

TRACHEAL INTUBATION DEVICE

This application claims priority to Canadian Patent Application No. 2,849,580, filed on Apr. 17, 2014 and entitled Tracheal Intubation Device, the entire contents of which are hereby incorporated by reference.

FIELD

The present invention relates to tracheal intubation devices, and more particularly, to a tracheal intubation device for placing a tracheal tube into a patient's trachea without direct or indirect visualization of the glottis.

BACKGROUND

Tracheal intubation is the placement of a tube in the trachea (windpipe) of a patient, which is necessary in many clinical situations to provide ventilation and oxygenation. For many decades, tracheal intubation has been performed under direct vision using a Macintosh laryngoscope, which has been considered the standard technique of intubation. Unfortunately, this approach to tracheal intubation has limitations. Intubation using this technique can be difficult and can, particularly in emergency situations, result in a high failure rate.

This has led to the development of alternative intubation devices and techniques using indirect vision, such as rigid and flexible endoscopes, video-laryngoscopes, and optical intubating stylets. Unfortunately, these devices are complex and expensive. Furthermore, in the presence of blood, secretions, and vomitus in the upper airway, as well as fogging of the lens or camera on the laryngoscope, it can be challenging to see the glottis (voice box) and the passage of the tracheal tube when employing the existing optical stylets and video scopes.

These difficulties have motivated the development of non-visual techniques, such as the light-guided intubation using a light-wand. The light-wand uses the principle of transillumination of the soft tissues of the neck, which was first described for nasotracheal intubation by Yamamura et al. in "*M. K. Device for blind nasal intubation*", Anesthesiology 1959; 20:221. The light-wand consists of a malleable stylet with a light-bulb at the distal tip, and a power source. The lighted tip of the light-wand is mounted inside the distal end of the tracheal tube so that it can be guided into the trachea using the light-glow—transillumination—at the anterior surface of the neck, taking the advantage of the superficial location of the trachea relative to the esophagus—food passage. When the tip of the lighted tracheal tube enters the glottis, a well-defined circumscribed glow can be readily seen slightly below the Adam's apple—thyroid prominence—of the anterior neck, while only a diffuse glow is visible when the lighted tracheal tube is in the esophagus. Using this technique, the practitioner can guide the tip of the tracheal tube easily and safely into the trachea without seeing the glottis.

Throughout the 1970s and 1980s, various versions of light-wand devices have been developed. However during use of these devices over the years substantial drawbacks have been identified such as:

poor light intensity; deterioration of light intensity in reusable incandescent devices with repeated usage and sterilization;

loss of the incandescent light bulb into the trachea;

heat injury to the airway mucosa from the incandescent light bulb;

inadequate length, limiting the use of the light-wand device to a shorter or cut tracheal tube;

rigidity of the light-wand, hampering use of the devices for light-guided nasal intubation; and inability of rigid light-wand devices to advance into the trachea beyond the glottis limiting their clinical utility to confirm correct tube placement into the trachea.

Some of these drawbacks have been overcome by the light-wand device disclosed in U.S. Pat. No. 5,163,841—and sold as TRACHLIGHT™ light-wand device—by providing an improved light source and added flexibility to the wand portion of the device. Unfortunately, the TRACHLIGHT™ light-wand device still has various drawbacks such as: use of an incandescent lightbulb having a fixed light intensity and generating a significant amount of heat; difficulties holding the trocar wire in place during oral intubation; deformation of the trocar wire with multiple use; and, absence of positive confirmation of correct tracheal tube placement.

It is desirable to provide a light-wand intubation device that enables respiratory gas monitoring during intubation for positive confirmation of correct tracheal tube placement.

It is also desirable to provide a light-wand intubation device that has a holding structure for holding a proximal end portion of a stylet placed in the light-wand in a first mode of operation and for enabling retracting or removing of the stylet from the light-wand in a second mode of operation.

It is also desirable to provide a light-wand intubation device having a light source that: produces substantially less heat than incandescent light; has adjustable light intensity; and, selectively provides white light or visible red light.

SUMMARY

Accordingly, one object of the present invention is to provide a light-wand intubation device that enables respiratory gas monitoring during intubation for positive confirmation of correct tracheal tube placement.

Another object of the present invention is to provide a light-wand intubation device that has a holding structure for holding a proximal end portion of a stylet placed in the light-wand in a first mode of operation and for enabling retracting or removing of the stylet from the light-wand in a second mode of operation.

Another object of the present invention is to provide a light-wand intubation device having a light source that: produces substantially less heat than incandescent light; has adjustable light intensity; and, selectively provides white light or visible red light.

According to one aspect of the present invention, there is provided an intubation device for placing a tracheal tube into a patient's trachea. The intubation device comprises a flexible light-wand having light emitting means placed in a distal end portion thereof. A distal portion of the flexible light-wand is adapted for placement inside the tracheal tube with the distal end portion thereof being in proximity to a distal end of the tracheal tube. The intubation device further comprises a coupling conduit. The coupling conduit has a tracheal tube port for being connected to the tracheal tube placed at a distal end thereof, a ventilating port for being connected to a ventilatory source, a monitoring port for being connected to a respiratory gas monitor, and a sealed aperture placed at a proximal end thereof. The sealed aperture accommodates the flexible light wand therethrough in a sealed fashion such that ventilating and monitoring of the patient is enabled while the flexible light-wand is placed in the tracheal tube.

According to another aspect of the present invention, there is provided an intubation device for placing a tracheal tube into a patient's trachea. The intubation device comprises a flexible light-wand having light emitting means placed in a distal end portion thereof. A distal portion of the flexible light-wand is adapted for placement inside the tracheal tube with the distal end portion thereof being in proximity to a distal end of the tracheal tube. A retractable stylet is placed inside the light-wand such that a distal end thereof is placed in the distal end portion of the flexible light-wand and a proximal end portion of the stylet is protruding the proximal end of the flexible light-wand. A holding structure is adapted to hold the proximal end of the tracheal tube and to hold the proximal end portion of the stylet such that the distal end portion of the light-wand is placed in proximity to the distal end of the tracheal tube in a first mode of operation and to enable retracting or removing the stylet in a second mode of operation.

According to yet another aspect of the present invention, there is provided an intubation device for placing a tracheal tube into a patient's trachea. The intubation device comprises a flexible light-wand having light emitting means placed in a distal end portion thereof. A distal portion of the flexible light-wand is adapted for placement inside the tracheal tube with the distal end portion thereof being in proximity to a distal end of the tracheal tube. The light emitting means emit light generated by at least a pulse width modulated light emitting diode. A holding structure is adapted to hold the proximal end of the tracheal tube and to hold the light-wand such that the distal end portion of the light-wand is placed inside a distal end portion of the tracheal tube. Electrical circuitry is connected to a power source and the light emitting diode. The electrical circuitry provides pulse width modulated electrical power to the light emitting diode.

One advantage of the present invention is that it provides a light-wand intubation device that enables respiratory gas monitoring during intubation for positive confirmation of correct tracheal tube placement.

A further advantage of the present invention is that it provides a light-wand intubation device that has a holding structure for holding a proximal end portion of a stylet placed in the light-wand in a first mode of operation and for enabling retracting or removing of the stylet from the light-wand in a second mode of operation.

A further advantage of the present invention is that it provides a light-wand intubation device having a light source that: produces substantially less heat than incandescent light; has adjustable light intensity; and, selectively provides white light or visible red light.

BRIEF DESCRIPTION OF THE DRAWINGS

An embodiment of the present invention is described below with reference to the accompanying drawings, in which.

DETAILED DESCRIPTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, certain methods and materials are now described.

Figure 1:
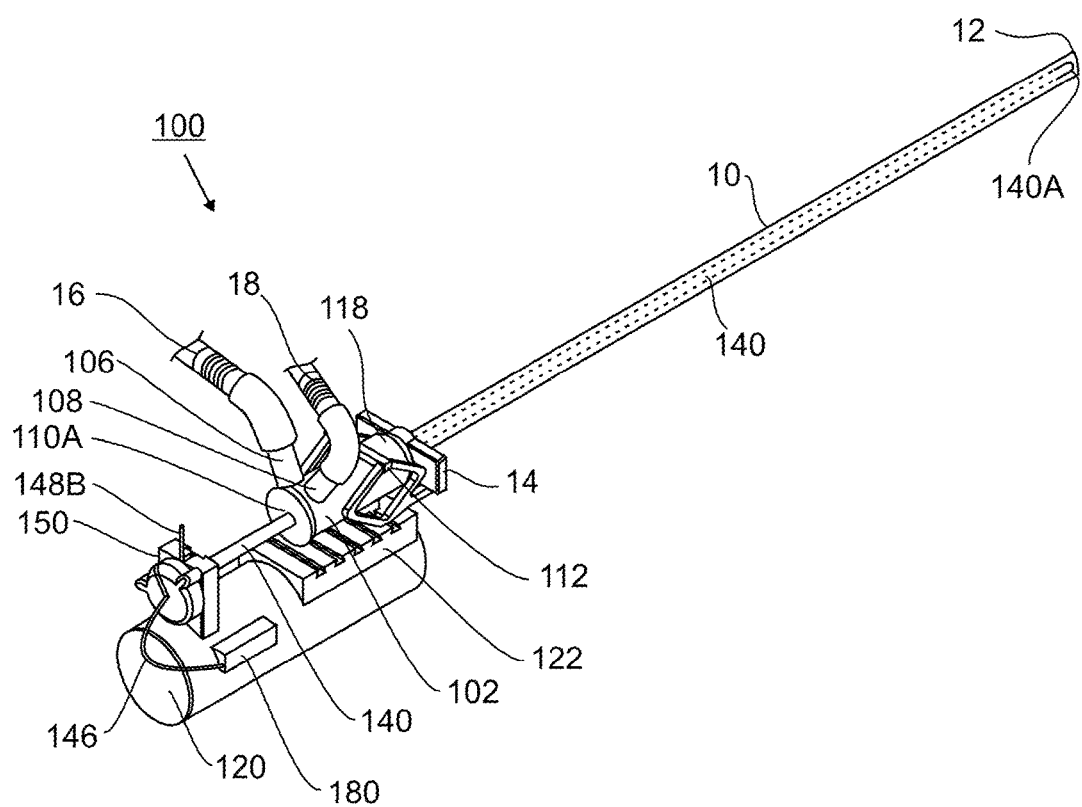
FIG. 1 is a simplified block diagram illustrating a perspective view of a light-wand intubation device according to an embodiment of the invention.

Referring to FIG. 1, an intubation device 100 according to an embodiment of the invention is provided. The intubation device 100 is adapted for placing a tracheal tube into a patient's trachea employing orotracheal as well as nasotracheal intubation. The intubation device 100 comprises a flexible light-wand 140 having light emitting means placed in a distal end portion 140A thereof, as will be described in more detail hereinbelow. A distal portion of the flexible light-wand 140 is adapted for placement inside the tracheal tube 10 with the distal end portion 140A thereof being in proximity to a distal end 12 of the tracheal tube 10. Coupling conduit 102 comprises, at a distal end thereof, tracheal tube port 118—in one case adapted for accommodating a male 15 mm standard endotracheal tube connector—for being connected to the tracheal tube 10 via tracheal tube connector 14. The coupling conduit 102 further comprises, at a proximal end portion thereof, ventilating port 108 for being connected to a ventilatory source via hose 18 and a monitoring port 106 for being connected to a respiratory gas monitor such as, for example, an End-Tidal Carbon Dioxide (ETCO$_2$) monitor via hose 16. The ventilating port 108 can be provided as a male 15 mm standard connector and the monitoring port 106 is provided as a standard Luer-lock female connector. Sealed aperture 110A is placed at a proximal end of the coupling conduit 102, as will be described in more detail hereinbelow. The sealed aperture 110A is adapted for accommodating the flexible light-wand 140 therethrough in a sealed fashion such that ventilating and monitoring of the patient is enabled while the flexible light-wand 140 is placed in the tracheal tube 10.

A stylet can be retractable and removable placed inside the flexible light-wand 140 such that a distal end thereof is placed in the distal end portion 140A of the flexible light-wand 140 and a proximal end portion 148B is protruding a proximal end of the flexible light-wand 140, as will be described in more detail hereinbelow.

Support structure 120 comprises: holding structure 150 for holding the proximal end portion 148B of the stylet and the proximal end portion of the flexible light-wand 140; and, holding structure 122 for holding the coupling conduit 102. The holding structure 150 is adapted for holding the proximal end portion 148B of the stylet such that the distal end portion 140A of the flexible light-wand 140 is placed in proximity to the distal end 12 of the tracheal tube 10 in a first mode of operation and for enabling retracting or removing the stylet in a second mode of operation. The holding structure 122 can be adapted for removable holding the coupling conduit, wherein a distance between the coupling conduit 102 and the proximal end of the flexible light-wand 140 is variable. The support structure 120 can comprise a housing containing a power source—for example, one or more AAA batteries—electronic control circuitry and user interface 180 and is shaped such that it can be used as a handle. The light emitting means comprise a LED placed in the distal end portion 140A of the flexible light-wand 140 connected to the electronic control circuitry via electric wiring 146 which is, in one case, removable connected to the electronic circuitry. Alternatively, the LED is placed in the housing and the light transmitted via an optical fiber having a distal end thereof placed in the distal end portion 140A of the flexible light-wand 140.

Figure 2A:
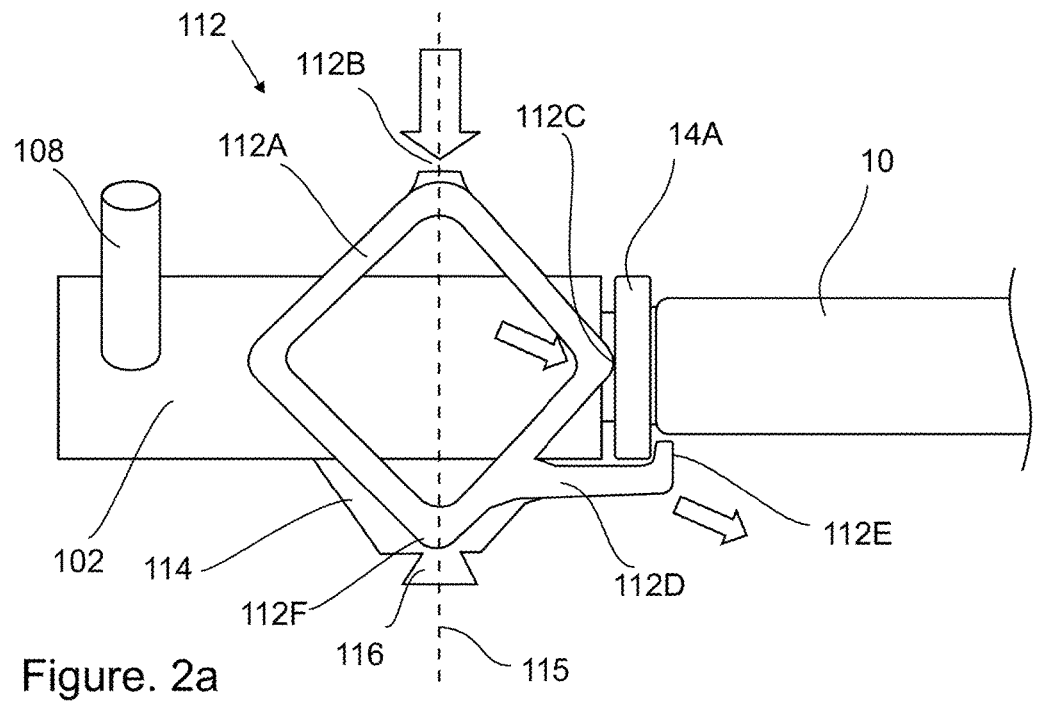
FIGS. 2a and 2b are simplified block diagrams illustrating a side view of a coupling conduit with a lock and quick release mechanism of the light-wand intubation device according to an embodiment of the invention, with the lock and quick release mechanism illustrated in a lock and a release position, respectively.
Figure 2B:
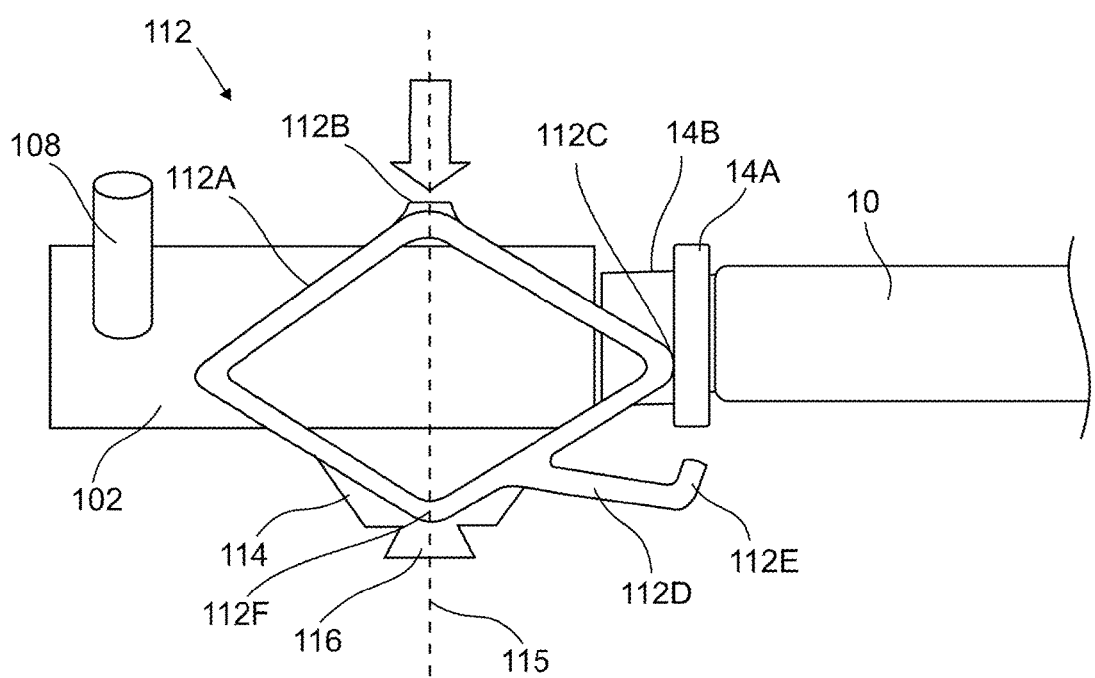
Figure 2C:
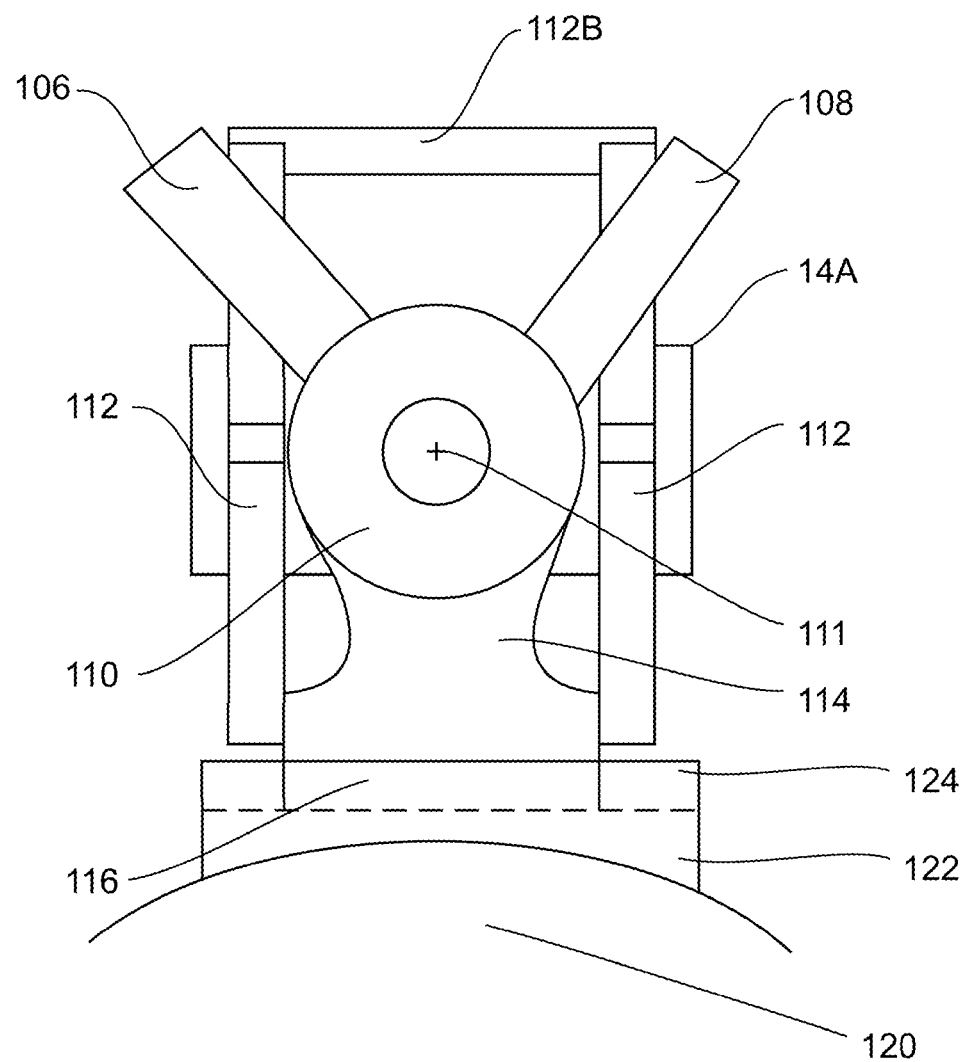
FIG. 2c is a simplified block diagram illustrating a rear view of the coupling conduit with the lock and quick release mechanism of the light-wand intubation device according to an embodiment of the invention.

Referring to FIGS. 2a to 2c, a lock and quick release mechanism 112 of the intubation device 100 according to an embodiment of the invention is provided. The lock and quick release mechanism 112 can comprise two rhombus shaped compression structures 112A placed on opposite sides of the coupling conduit 102 and fixedly mounted at a bottom portion 112F thereof to holding element 114 of the coupling conduit 102. The compression structures 112A are connected at the top via connecting bar 112B. Each compression structure 112A comprises locking arm 112D with locking element 112E. In locking mode, illustrated in FIG. 2a, the locking element 112E interacts with holding element 14A of the tracheal tube connector 14 and abuts the same in a coupled position with the coupling conduit 102. For quick releasing the tracheal tube connector 14 from the coupling conduit 102, the practitioner compresses the compression structures 112A by applying pressure onto the connecting bar 112B, as indicated by the block arrow, thus compressing the compression structures 112A causing interacting joint 112C and locking arm 112D with locking element 112E to move in a distal and downward direction, as indicated by the block arrows. The movement of the interacting joint 112C ejects the tracheal tube connector 14 from the coupling conduit 102 by pushing the holding element 14A in the distal direction, as illustrated in FIG. 2b. For connecting the tracheal tube connector 14 to the coupling conduit 102, the practitioner compresses the compression structures 112A inserts the tracheal tube connector 14 into the tracheal tube port of the coupling conduit 102 and releases the compression structures 112A. The lock and quick release mechanism 112 can be adapted to enable the practitioner to operate the same with one hand, for example, by pressing the connecting bar 112B with the thumb while holding the support structure 120 of the intubation device 100 with the other fingers. The lock and quick release mechanism 112 is made, for example, as a single piece of an elastic material. Various plastic materials, for example, Nylon, have sufficient strength for locking the tracheal tube connector 14 as well as sufficient elasticity to enable able compression for ejecting the tracheal tube connector 14 and allow manufacture of the lock and quick release mechanism 112 using conventional plastic manufacturing processes. The lock and quick release mechanism 112 is fixedly mounted to the holding element 114 in a conventional manner using, for example, an adhesive. The lock and quick release mechanism 112 can be designed such that pressure applied to the connecting bar 112B acts along line 115 through connecting element 116 for connecting the coupling conduit 102 to the holding structure 122. Of course, other mechanisms may be used for providing a lock and quick release of the tracheal tube connector 14. For example, the lock and quick release mechanism 112 may be provided as a spring loaded lever mechanism comprising the locking arm with the locking element and the interacting joint.

Figure 2D:
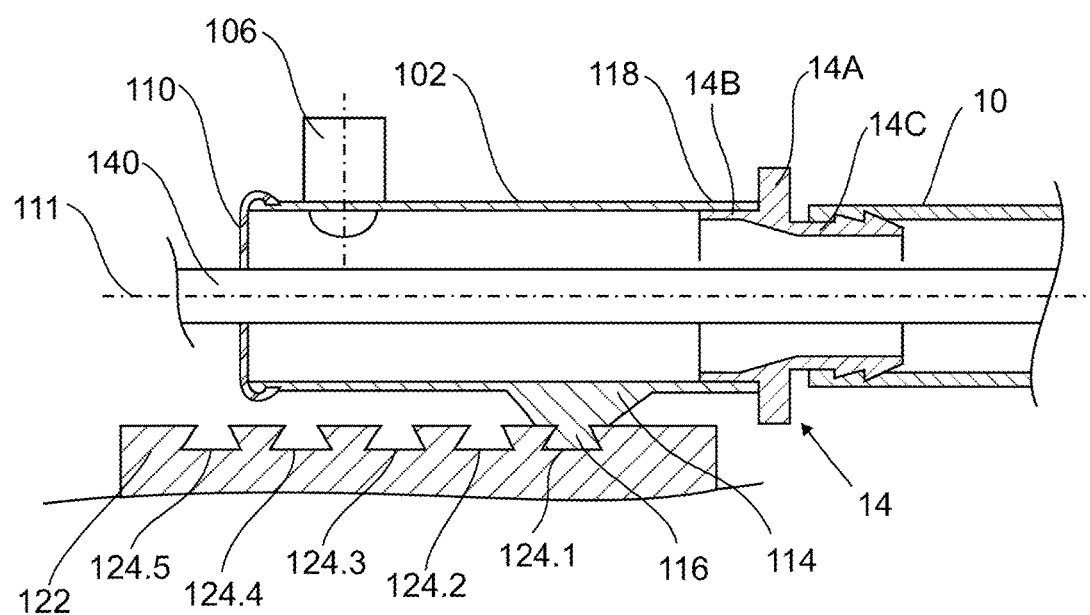
FIG. 2d is a simplified block diagram illustrating a cross sectional view of the coupling conduit with the tracheal tube coupled thereto of the light-wand intubation device according to an embodiment of the invention.

FIG. 2d illustrates a cross sectional view of the coupling conduit 102 with the tracheal tube 10 coupled thereto. The male connecting element 14B of the tracheal tube connector 14—having tracheal tube 10 mounted thereto via tapered friction mounting element 14C—is coupled to the respective female tracheal tube port 118. The flexible light-wand 140 is provided through the sealed aperture 110A of end cap 110 and placed inside the coupling conduit 102 and the tracheal tube 10 oriented along longitudinal axis 111. The coupling conduit 102, the holding element 114, and the connecting element 116 are, in one case, made as a single unit made of a suitable plastic material such as, for example, Nylon or PVC using conventional plastic molding techniques. The connecting element 116 can be provided as a dove tail shaped ridge oriented substantially perpendicular to the longitudinal axis 111 which is inserted into one of respective dove tail shaped grooves 124.1, 124.2, 124.3, 124.4, 124.5 of the holding structure 122.

Figure 2E:
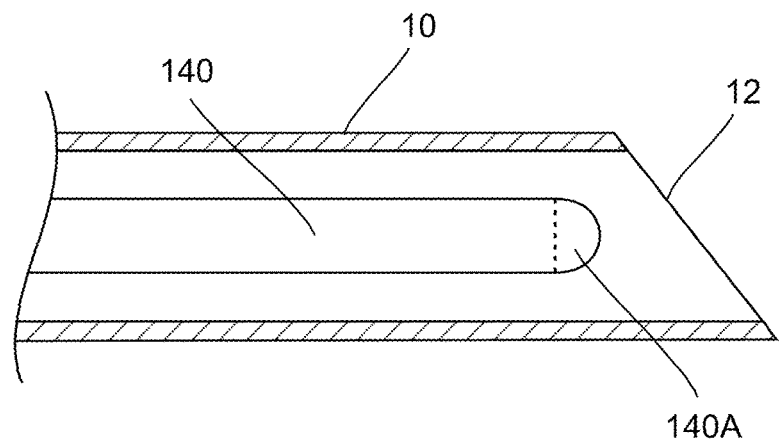
FIG. 2e is a simplified block diagram illustrating a cross sectional view of the light-wand of the light-wand intubation device according to an embodiment of the invention placed in the tracheal tube.
Figure 2F:
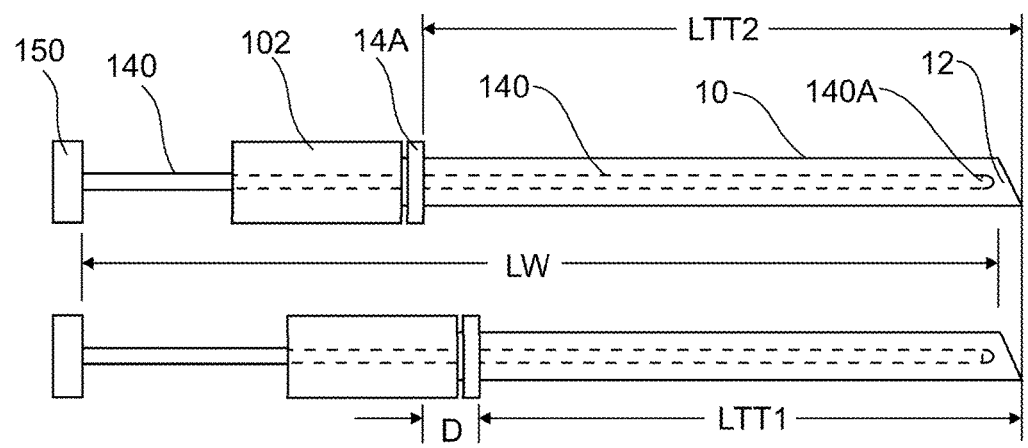
FIGS. 2f and 2g are simplified block diagrams illustrating adjustment of the light-wand intubation device according to an embodiment of the invention to accommodate tracheal tubes having different lengths.
Figure 2G:
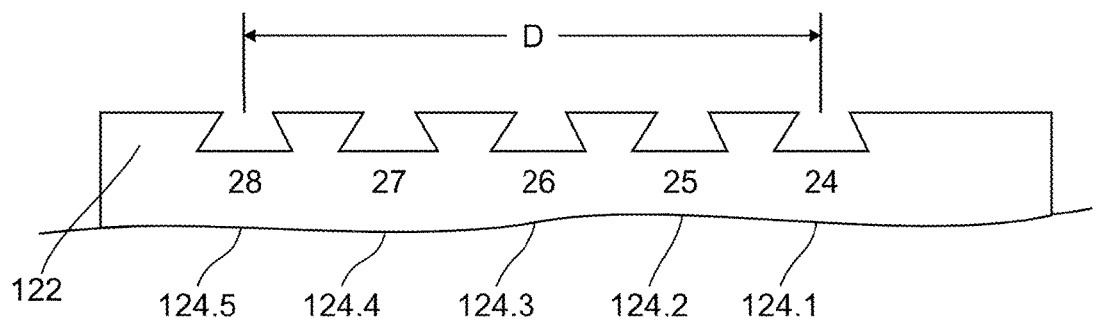

Referring to FIGS. 2e to 2g, standard tracheal tubes are provided having different lengths, typically varying between length LTT1 of 24 cm and LTT2 of 28 cm in increments of 1 cm. In order to ensure that the distal end portion 140A of the flexible light-wand 140 having a fixed length LW is always placed in proximity to the distal end 12 of the tracheal tube 10 for the different lengths of the tracheal tube 10, as illustrated in FIGS. 2e and 2f, the position of the coupling conduit 102 with respect to the holding structure 150 is adjusted by inserting the connecting element 116 into one of the grooves 124.1, 124.2, 124.3, 124.4, and 124.5, with grooves 124.1 and 124.5 spaced apart the distance D between LTT1 and LTT2 and grooves 124.2, 124.3, and 124.4 spaced in 1 cm increments, as illustrated in FIG. 2g. To facilitate adjustment, each groove is indicated with the respective length of the tracheal tube 10.

Figure 3A:
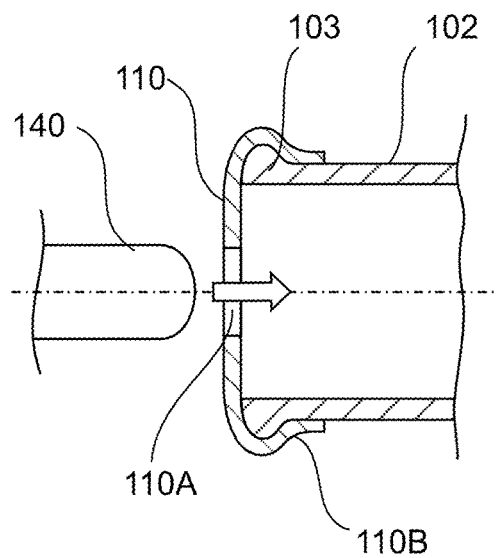
FIGS. 3a to 3d are simplified block diagrams illustrating cross sectional views of a sealed aperture of the light-wand intubation device according to an embodiment of the invention.
Figure 3B:
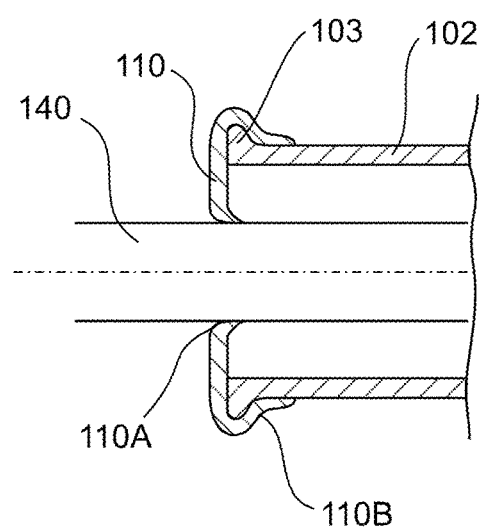
Figure 3C:
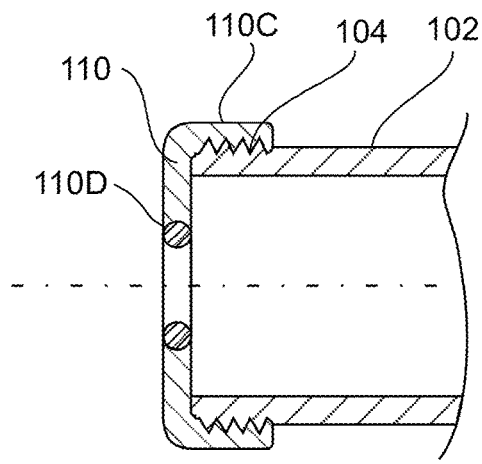
Figure 3D:
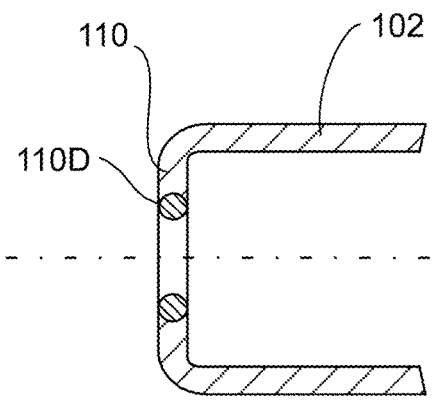

To enable ventilating and monitoring of the patient while the flexible light-wand 140 is placed in the tracheal tube 10, the sealed aperture 110A is provided for accommodating the flexible light-wand 140 therethrough in a sealed fashion. Referring to FIGS. 3a and 3b, a flexible end cap 110 made of a flexible sheet material such as, for example, a rubber material, is mounted to the proximal end of the coupling conduit 102. The end cap 110 comprises sealed aperture 110A which is sized such that a seal is provided when the flexible light-wand 140 is placed therethrough, as illustrated in FIGS. 3a and 3b. The end cap 110 is mounted to the proximal end of the coupling conduit 102 via mounting portion 110B thereof and holding rim 103 of the coupling conduit 102. The mounting portion 110B is sized to provide a snug and sealing fit between the end cap 110 and the coupling conduit 102. Optionally, the holding rim 103 is omitted. Alternatively, the end cap 110 is rigid with an O-ring seal 110D, as illustrated in FIG. 3c. The rigid end cap 110 is mounted to the coupling conduit 102, for example, via a threaded portion 110C interacting with a respective thread 104 placed at the proximal end of the coupling conduit 102. Further alternatively, the coupling conduit 102 comprises a proximal end wall 110 having an aperture with an O-ring seal 110D placed therein, as illustrated in FIG. 3d.

Figure 4A:
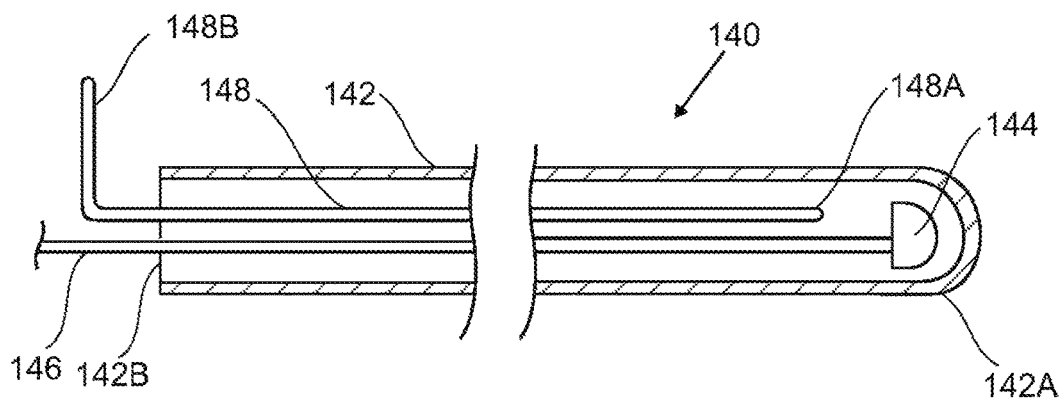
FIGS. 4a to 4d are simplified block diagrams illustrating cross sectional views of different light-wands of the light-wand intubation device according to an embodiment of the invention.
Figure 4B:
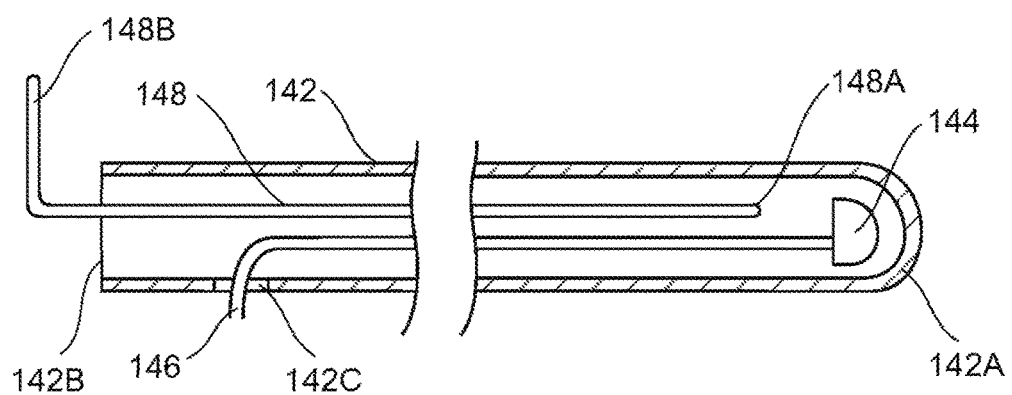

In order to enable employment of the intubation device 100 for orotracheal as well as nasotracheal intubation, the flexible light-wand 140 has to be sufficiently stiff for the orotracheal intubation as well as sufficiently flexible for the nasotracheal intubation. To this end the flexible light-wand 140 is designed to be sufficiently flexible for the nasotracheal intubation and can be made sufficiently stiff for the orotracheal intubation by inserting a stylet therein. Referring to FIGS. 4a and 4b, the flexible light-wand 140 comprises a flexible sheath 142 containing a light source such as a LED placed in a distal end portion 142A of the sheath 142. Electrical power is provided via wiring 146 which protrudes the proximal end 142B of the sheath 142, as illustrated in FIG. 4a, or opening 142C, as illustrated in FIG. 4b. The sheath 142 and the wiring 146 are sufficiently flexible to enable nasotracheal intubation. The sheath 142 is made of, for example, a sufficiently flexible and transparent plastic material such as a suitable PVC material. The sheath can be made of a latex-free material. The sheath 142 can comprise a low friction coating—for example, TEFLON® material coating—to easily slide inside the tracheal tube 10 or, alternatively, is made of a TEFLON material. Sufficient stiffness for orotracheal intubation is provided by placing stylet 148 inside the sheath 142 with a proximal end portion 148B protruding the proximal end 142B of the sheath and a distal end 148A placed in proximity the distal end portion 142A of the sheath 142. The stylet 148 can comprise a low friction coating—for example, TEFLON material coating—to easily slide inside the sheath 142. The sheath 142 protects the LED, the wiring, and the stylet from protein contamination and is, for example, provided as a throw-away component for one-time use.

Figure 4C:
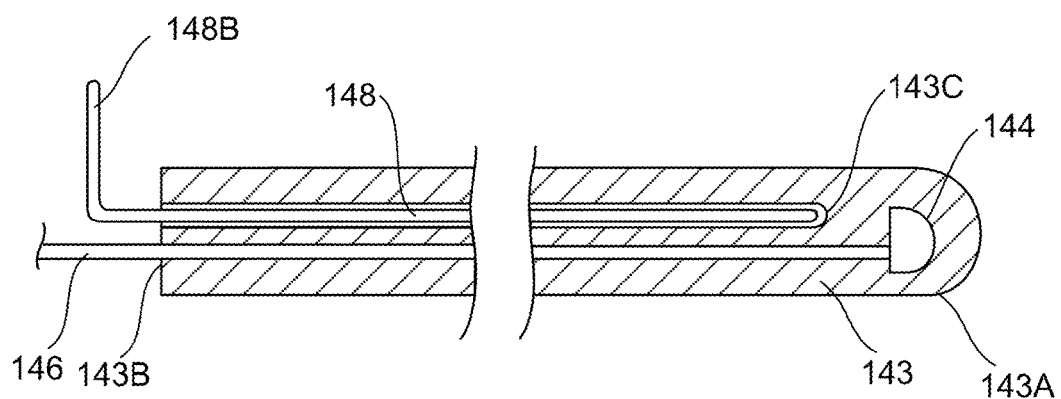

Alternatively, the wiring and the LED are encased in flexible wand 143 with the LED being placed in distal end portion 143A of the wand 143 and the wiring protruding the proximal end 143B of the wand 143, as illustrated in FIG. 4c. The wand 143 further comprises bore 143C for accommodating the stylet 148 therein. The sheath 143 is made of, for example, a sufficiently flexible and transparent plastic material such as a suitable PVC material.

Figure 4D:
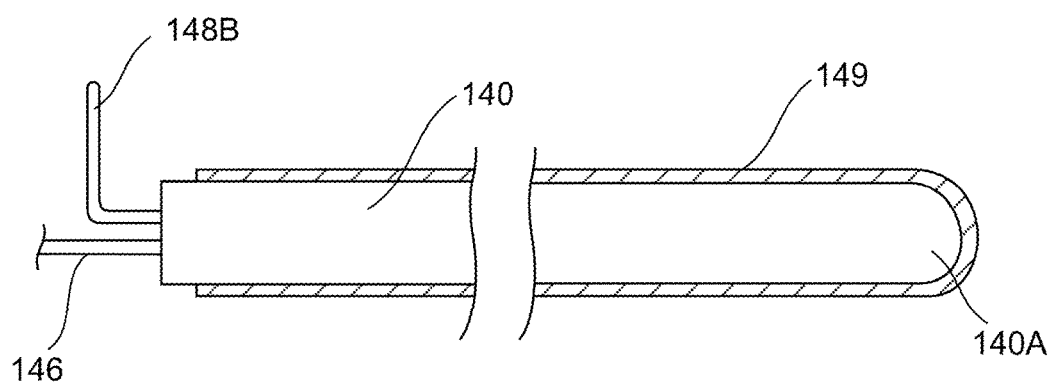

Further alternatively, the flexible wand 140 is provided with a throw-away protective cover 149 for one-time use, as illustrated in FIG. 4d. The cover 149 is made of, for example, a sufficiently flexible and transparent plastic material such as a suitable PVC or PolyURethane (PUR) material and applied in a condom-like fashion.

Figure 5A:
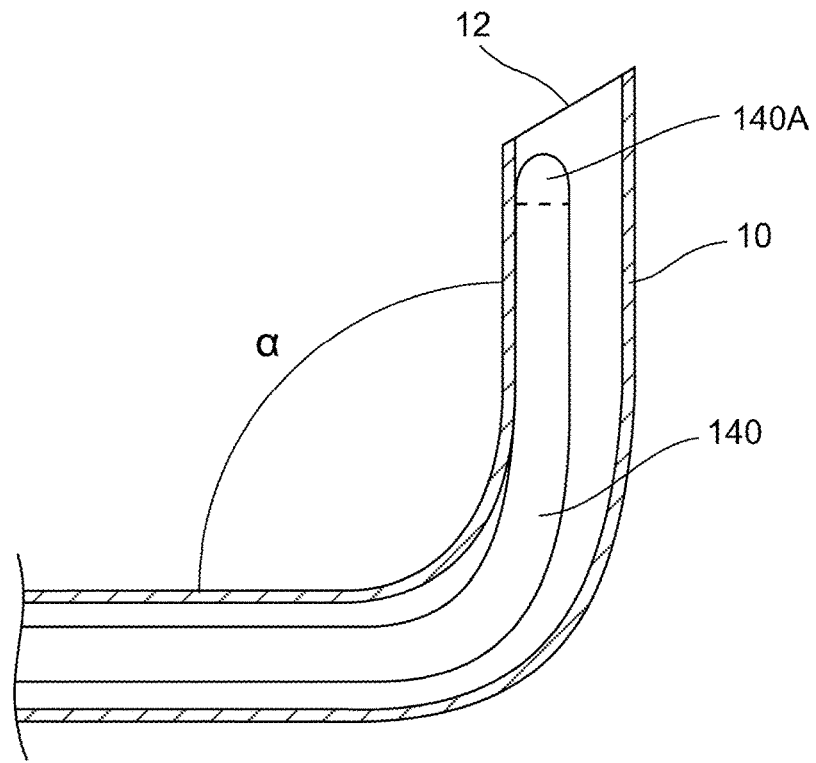
FIG. 5a is a simplified block diagram illustrating a cross sectional view of the light-wand of the light-wand intubation device according to an embodiment of the invention placed in the tracheal tube with the light-wand and the tracheal tube being bent for orotracheal intubation.
Figure 5B:
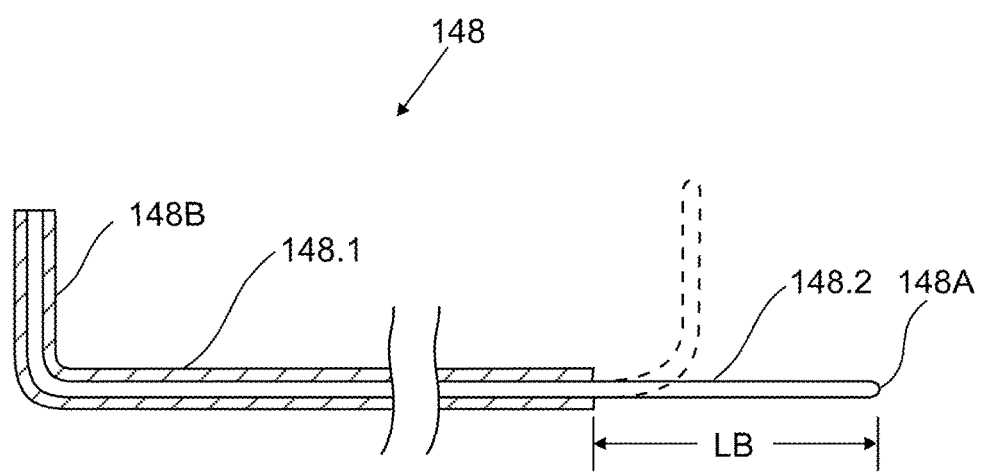
FIGS. 5b to 5d are simplified block diagrams illustrating cross sectional views of different stylets of the light-wand intubation device according to an embodiment of the invention.
Figure 5C:
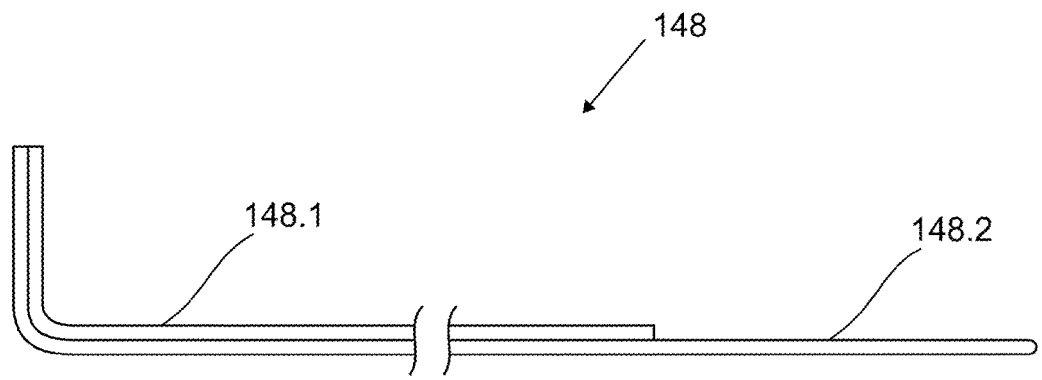
Figure 5D:
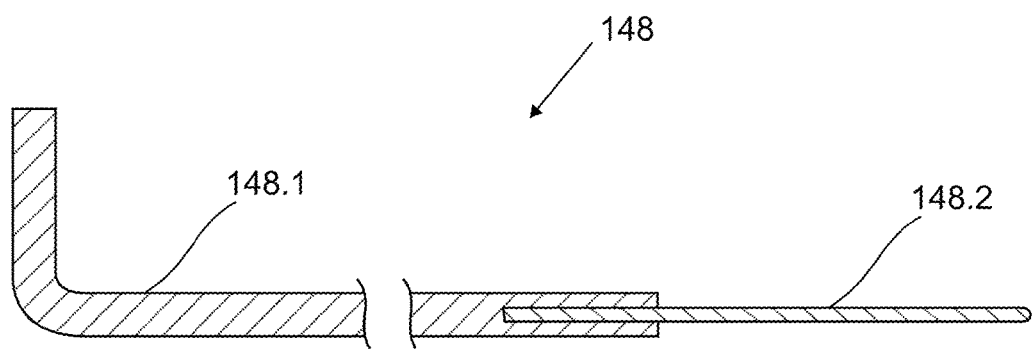

For orotracheal intubation the distal end portion of the tracheal tube 10 is bent, as illustrated in FIG. 5a, forming a user determined angle α—typically, of approximately 90°—enhancing maneuverability during intubation and facilitating placement of the tracheal tube 10 through the patient's glottis. As illustrated in FIG. 5b, the stylet 148 of the intubation device 100 comprises a proximal section 148.1 that is substantially stiff and a distal section 148.2 that is malleable and sufficiently strong to hold the flexible wand 140 and the tracheal tube 10 at the 90° angle. The distal section 148.2 can have a length LB equivalent to the length required for bending the tracheal tube 10 of approximately 6-10 cm. The stylet 148 is made of a wire forming the distal section 148.2 which is inserted and hold in a hollow cylinder forming the proximal section 148.1. The wire and the hollow cylinder are made of, for example, a suitable metal such as stainless steel. The stylet 148 can comprise a low friction coating—for example, TEFLON material coating. The proximal end portion 148B of the stylet 148 is bent, in one case forming a 90° angle, for fixedly holding the same at holding structure 150. Alternatively, the stylet 148 comprises two sections—having, for example, rectangular cross sections—which are mounted to each other using, for example, an adhesive, as illustrated in FIG. 5c. For example, the proximal section 148.1 is sufficiently stiff and made of a suitable plastic material such as Nylon or PVC, while the distal section is malleable and made of a suitable metal such as stainless steel sheet material. Further alternatively, the stylet 148 comprises a proximal section 148.1 that is sufficiently stiff and made of a suitable plastic material such as Nylon or PVC. The distal section 148.2 is malleable and made of a suitable metal such as stainless steel and inserted into a distal end portion of the proximal section 148.1, as illustrated in FIG. 5d.

Figure 6A:
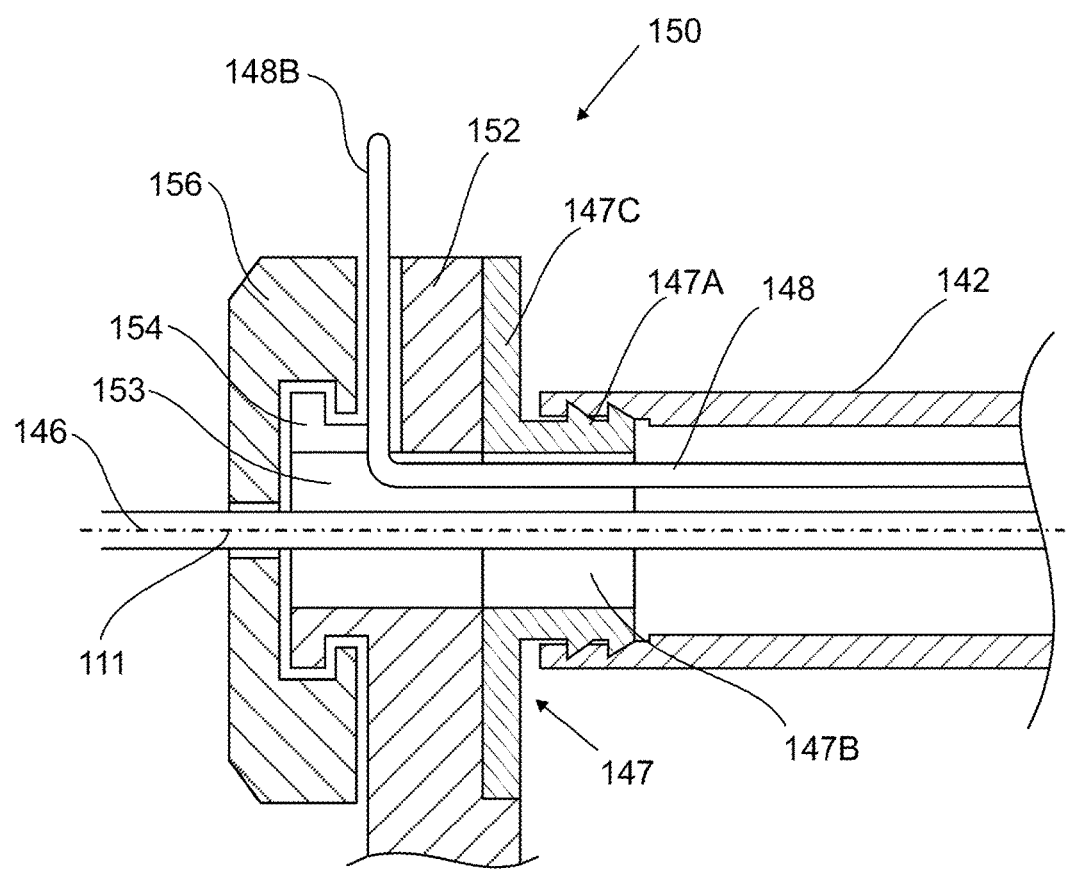
FIGS. 6a to 6e are simplified block diagrams illustrating a cross sectional view, a rear view, a front view, a top view, and another rear view, respectively, of a holding structure for holding the stylet of the light-wand intubation device according to an embodiment of the invention.
Figure 6B:
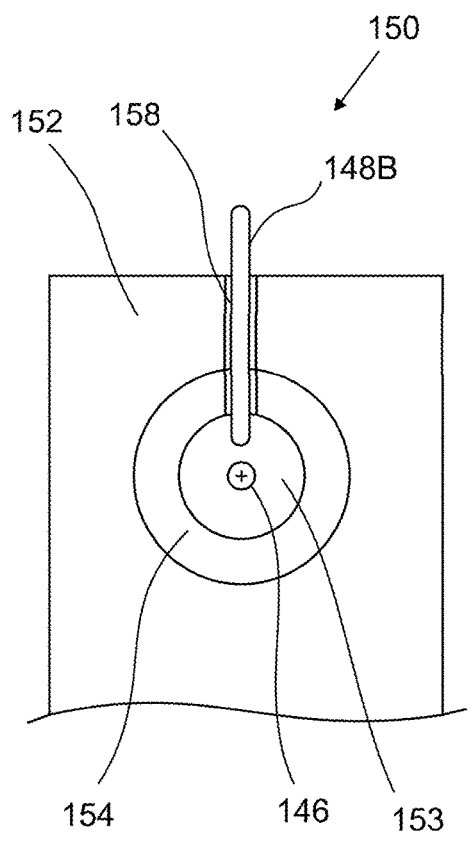
Figure 6C:
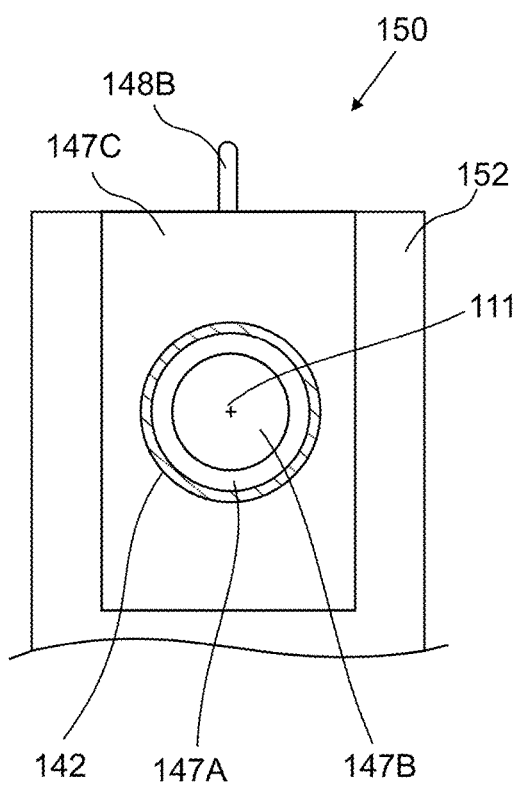
Figure 6D:
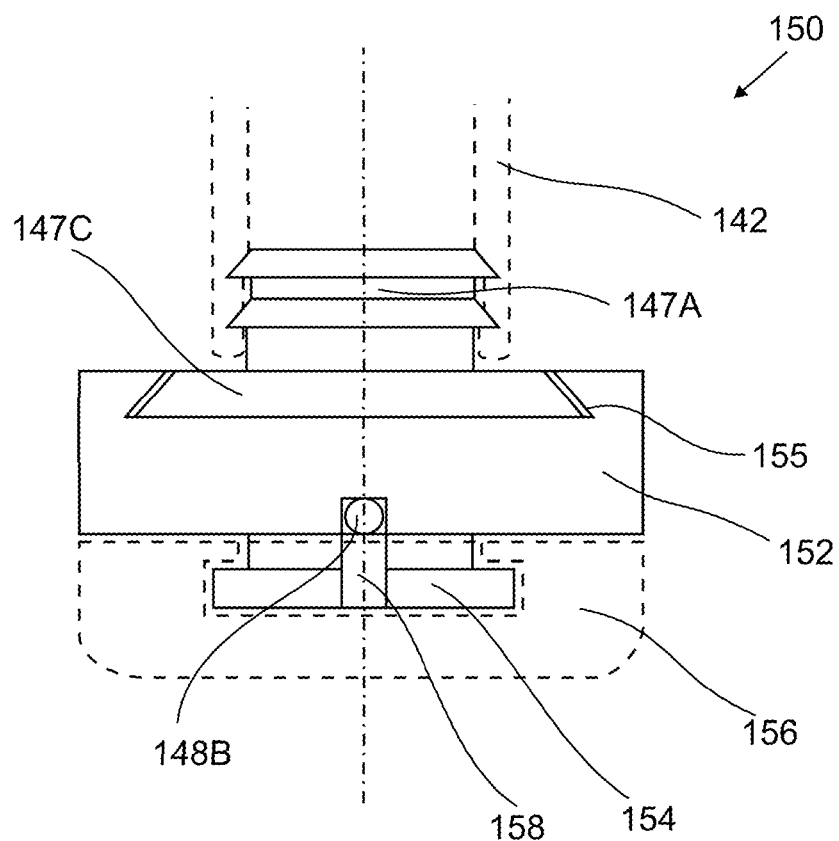
Figure 6E:
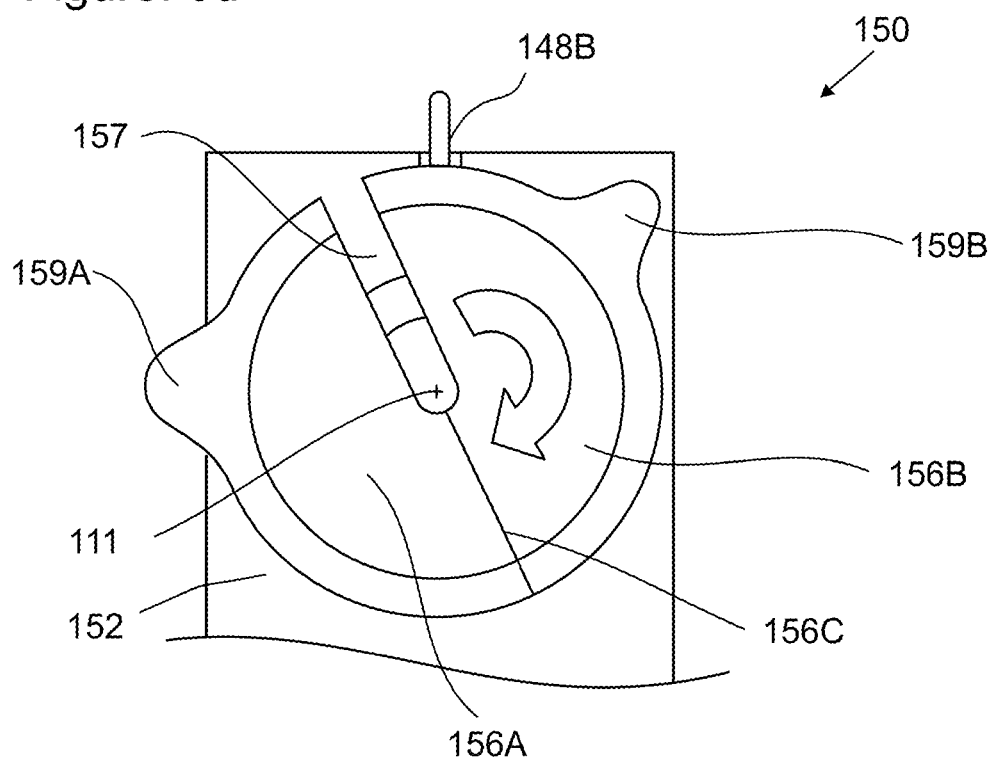

The holding structure 150 of the intubation device 100, illustrated in FIGS. 6a to 6e, comprises central element 152 having bore 153—oriented along longitudinal axis 111—placed therein. The bore 153 enables accommodation of the stylet 148 and the wiring 146 therethrough. The holding structure 150 holds the proximal end portion 148B of the stylet 148 in groove 158 placed in the central element 152 in concert with knob 156 which is rotatable about axis 111 mounted to knob holding element 154 of the central element 152, as illustrated in FIGS. 6a and 6e. For retracting and removing the stylet 148, the knob 156 is turned such that slot 157 placed in the knob 156 coincides with the proximal end portion 148B of the stylet 148 allowing movement of the same therethrough. The knob 156 comprises, for example, two sections 156A and 156B which are adhered to each other after mounting to the knob holding element 154 at connection 156C. The knob 156 can comprise two protrusions 159A and 159B placed on opposite sides of the slot 157 for facilitating turning of the same for left handed or right handed use. The sheath 142 of the light-wand 140 is mounted to the holding structure 150 via wand coupler 147. The wand coupler 147 is mounted to the sheath 142 via hose barbs of wand mounting element 147A. The wand coupler 147 has bore 147B—oriented along longitudinal axis 111—placed therein. The bore 147B enables accommodation of the stylet 148 and the wiring 146 therethrough. The wand coupler 147 is removable mounted to the central element 152 via coupling element 147C inserted in respective groove 155 placed in the central element 152. The coupling element 147C and the respective groove 155 can be dove tail shaped. Alternatively, the proximal end portion of the sheath 142 is shaped such, for example, forming a flange, that it can be inserted in the groove 155, thus omitting wand coupler 147.

In children or extremely thin patients, the thickness of the soft tissues from the surface of the skin to the inner wall of the trachea is small compared to the average adult population while on the other hand in obese patients the thickness of the soft tissues from the surface of the skin to the inner wall of the trachea is large compared to the average adult population. Use of a single light source having a fixed intensity, for example, adapted for use in an average adult, can result in serious limitations during intubation of children or obese patients such as observed transillumination while the tracheal tube with the light-wand is inserted into the esophagus in children or no transillumination is observed in obese patients despite correct placement of the tip of the tracheal tube.

Figure 7A:
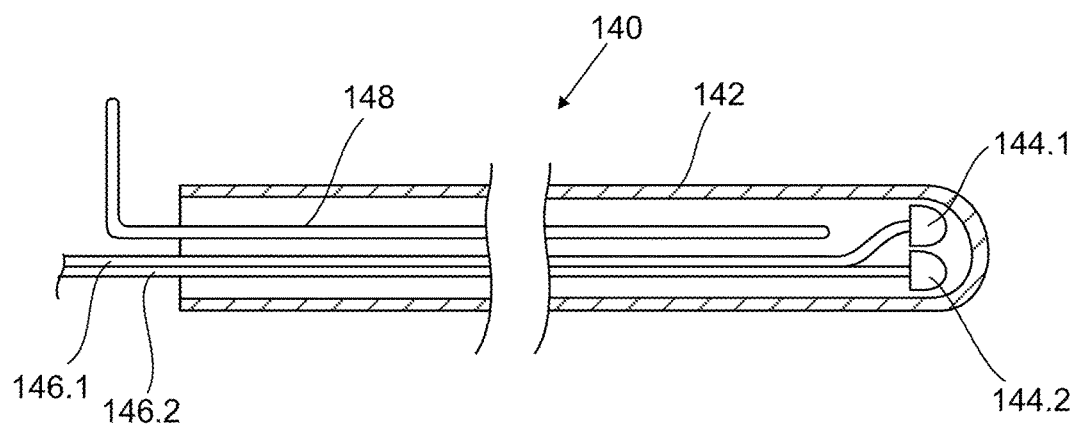
FIG. 7a is a simplified block diagram illustrating a cross sectional view of a light-wand having two LEDs of the light-wand intubation device according to an embodiment of the invention.

As illustrated in FIG. 7a, two LEDs 144.1 and 144.2 can be placed in the light-wand 140 of the intubation device 100 with respective wiring 146.1 and 146.2. The LED 144.1 is capable of emitting white light while the LED 144.2 is capable of emitting visible red light. The visible red light provides best depth of penetration in skin and may be used, for example, in obese patients.

A light source dimmer can be employed to reduce the intensity of the light source using Pulse Width Modulation (PWM), providing flexibility to adjust to optimal light intensity during tracheal intubation in different patient populations. Using the LEDs in PWM mode reduces the heat generated compared to use in Continuous Wave (CW) mode and allows adjustment of the pulse width to maximize tissue penetration while dimming is then achieved by changing the pulse width such that the intensity of the transmitted light is reduced.

Figure 7B:
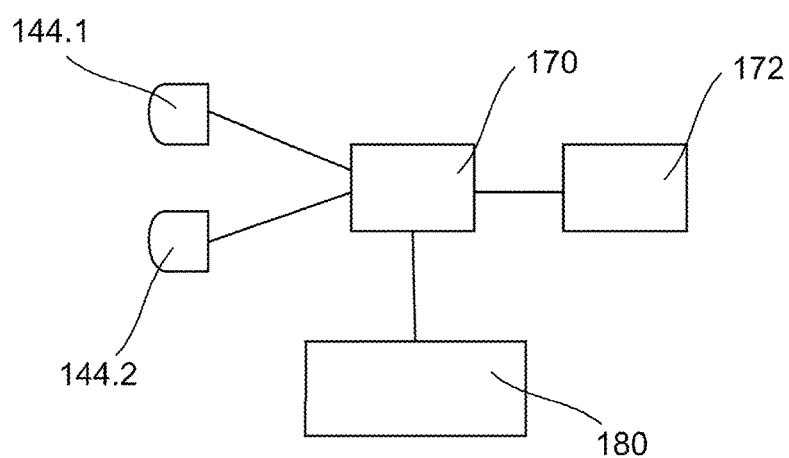
FIG. 7b is a simplified block diagram illustrating electric control circuitry of the light-wand intubation device according to an embodiment of the invention.
Figure 7C:
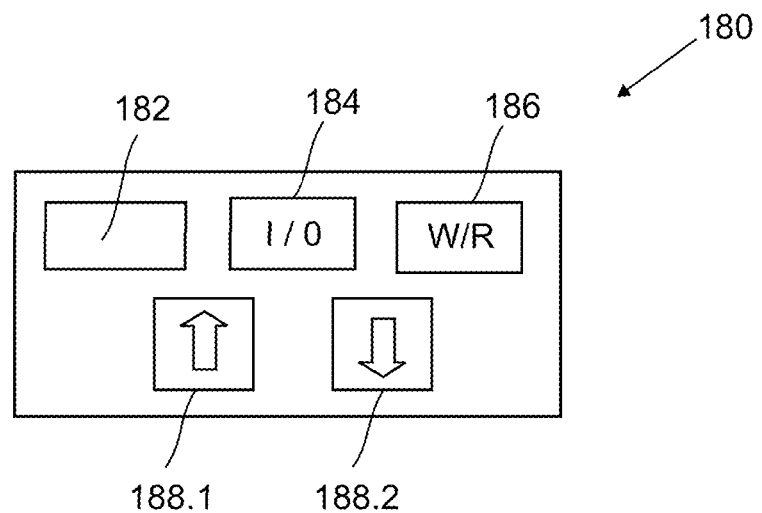
FIG. 7c is a simplified block diagram illustrating a user interface of the light-wand intubation device according to an embodiment of the invention.

Referring to FIG. 7b, a control circuit for controlling provision of light in the intubation device 100 is provided. Microcontroller 170 is connected to power source 172, to user interface 180 and LEDs 144.1, 144.2. The power source 172 is, for example, one or more batteries. The microcontroller 170 receives the electrical power from the power source 172 and provides PWM power to one of the LEDs 144.1, 144.2 in dependence upon user input received from the user interface 180. The user interface 180, illustrated in FIG. 7c, comprises, for example, a battery charge indicator 182 and push buttons: 184 for switching the device ON/OFF; 186 for selecting RED or WHITE light; 188.1 for increasing the intensity; and, 188.2 for decreasing the intensity. Dimming of LEDs using PWM is well known in the art and numerous state of the art microcontrollers provide a PWM output signal.

Figure 8A:
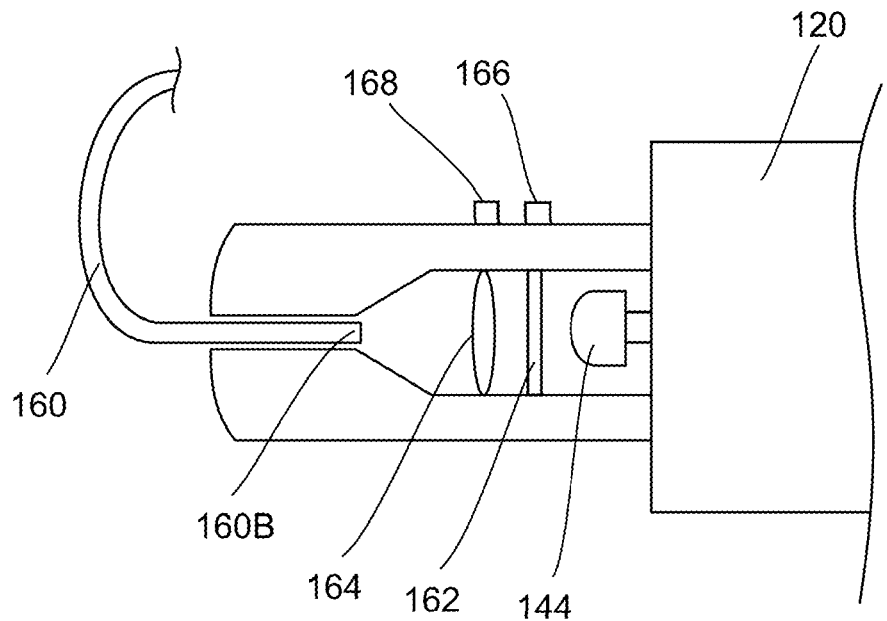
FIGS. 8a and 8b are simplified block diagrams illustrating cross sectional views of a coupler for coupling light into an optical fiber and an optical fiber placed in the light-wand, respectively, of the light-wand intubation device according to another embodiment of the invention.
Figure 8B:
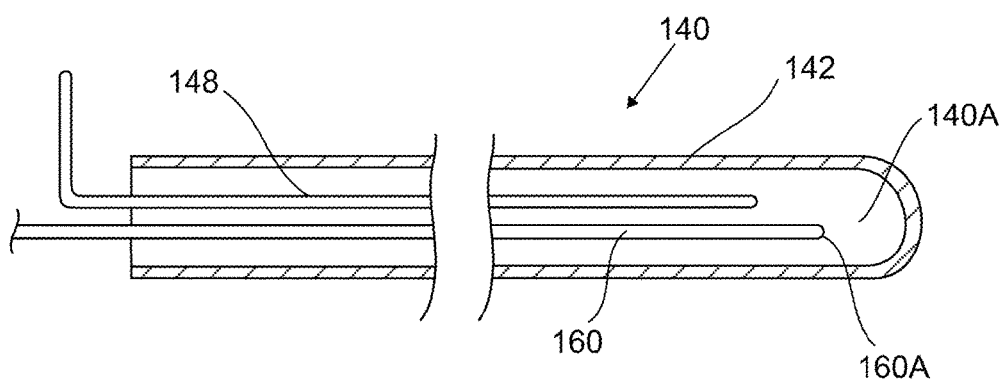

In an alternative embodiment, a light source 144 is, for example, placed in the housing of the support structure 120 and the light is transmitted via optical fiber 160, as illustrated in FIGS. 8a and 8b. The light source 144 is, for example, a LED or an incandescent light-bulb. A distal section of the optical fiber 160 is placed in the light-wand 140 with a distal end 160A thereof being placed in the distal end portion 140A of the light wand 140. Light emitted from the light source 144 is: focused into the optical fiber 160 at the proximal end 160B thereof via collator lens 164; transmitted through the optical fiber 160; and, emitted from the distal end 160A of the optical fiber 160. The light source 144 is provided, for example, as a white light source and provision of visible red light is then realized by interposing red filter 162 between the light source 144 and the collator lens 164 using selector knob 166. The light intensity is changed, for example, by slightly defocussing the light provided to the proximal end 160B of the optical fiber 160, i.e. moving the collator lens 164 to change the distance between the collator lens 164 and the proximal end of the optical fiber 160 using knob 168. Alternatively, two LEDs 144.1 and 144.2 emitting white and visible red light are provided, together with the control circuitry illustrated in FIG. 7b for selecting white or visible red light and for dimming the light intensity.

For example, prior and during orotracheal intubation using the device 100, the following steps are performed:

connecting the light-wand 140 to the holding structure 150 by passing the wiring 146 through bore 153 and inserting wand coupler 147 into groove 155 placed in the central element 152 of the holding structure 150;

connecting the tracheal tube 10 to the coupling conduit 102 using lock and quick release mechanism 112;

passing the light-wand 140 through the sealed aperture 110A, the coupling conduit 102 into the tracheal tube 10;

mounting the coupling conduit 102 to the holding structure 122 by inserting the connecting element 116 into one of the respective dove tail shaped grooves 124.1, 124.2, 124.3, 124.4, 124.5 corresponding to the length of the tracheal tube;

inserting the stylet 148 into the light-wand 140 and the proximal end portion 148B thereof into groove 158 placed in the central element 152 of the holding structure 150 and turning the knob 156 for locking the stylet 148, thus preventing retraction of the wire stylet 148 under axial loading conditions during bending of the stylet and intubation;

bending the distal end portion of the tracheal tube with the light-wand 140 and the stylet 148 placed therein to form an approximately 90° angle;

switching light on, selecting white or red light, and adjusting the intensity;

passing the tracheal tube 10 through the oral cavity into the patient's oropharunx until the glottic opening is reached;

turning knob 156 to center position and retracting the wire stylet 148 a distance of approximately 10 cm, thus making the distal end portion of the tracheal tube 10 with the light-wand 140 therein more flexible for further advancement through the glottic opening into the trachea;

optionally, adjusting the light intensity during the insertion of the tracheal tube 10 with the light-wand 140 therein;

observing the transillumination during the insertion of the tracheal tube 10 with the light-wand 140 therein;

after placement of the tracheal tube 10 with the light-wand 140 therein, connecting the ventilating port 108 to the ventilatory source and the monitoring port 106 to the $ETCO_2$ monitor;

observing the transillumination and the $ETCO_2$ monitor for positive confirmation of the accurate placement of the tracheal tube 10; and after positive confirmation, ejecting the tracheal tube 10 from the coupling conduit 102 using lock and quick release mechanism 112, disconnecting the ventilatory source and the monitor from the coupling conduit 102 and removing the device 100.

The present invention has been described herein with regard to certain embodiments. However, it will be obvious to persons skilled in the art that a number of variations and modifications can be made without departing from the scope of the invention as described herein.

What is claimed is:

1. An intubation device for placing a tracheal tube into a patient's trachea comprising:
    a flexible light-wand having light emitting means placed in a distal end portion thereof and a light-wand coupler at a proximal end thereof, a distal portion of the flexible light-wand being adapted for placement inside the tracheal tube with the distal end portion thereof being in proximity to a distal end of the tracheal tube;
    a stylet retractable and removable placed inside the flexible light-wand such that a distal end portion thereof is placed in the distal end portion of the flexible light-wand and a proximal end portion is protruding the light-wand coupler, the proximal end portion of the stylet being adapted for being accommodated in a first holding structure, the distal end portion of the stylet being malleable and sufficiently strong to hold the distal end portion of the flexible light-wand and a distal end portion of the tracheal tube at an approximately 90° angle during intubation procedures;
    a coupling conduit, the coupling conduit having:
        a connecting element; and
        a tracheal tube port placed at a distal end thereof, the tracheal tube port for being connected to the tracheal tube; and
    a support structure having the first holding structure at a first end portion thereof and a second holding structure at a second opposite end portion thereof, the first holding structure being adapted for being removable coupled with the light-wand coupler, the second holding structure for being removable coupled with the connecting element, the support structure extending continuously between the first holding structure and the second holding structure and the first holding structure and the second holding structure having a predetermined distance therebetween such that in operation the distal end portion of the light-wand is in proximity to the distal end of the tracheal tube wherein the second holding structure comprises a plurality of interacting elements, each interacting element for being removable coupled with the connecting element, each interacting element being placed at a predetermined location spaced apart from the location of each adjacent interacting element along a direction parallel to a longitudinal axis through the light-wand, the coupling conduit, and the tracheal tube, each location being associated with a predetermined distance between the coupling conduit and the proximal end of the flexible light-wand corresponding to a length of a tracheal tube of a plurality of tracheal tubes having different lengths such that in operation the distal end portion of the light-wand having a same length is in proximity to the distal end of each tracheal tube of the plurality of tracheal tubes.

2. The intubation device according to claim 1 wherein the first holding structure is adapted for holding the proximal end portion of the stylet such that the distal end portion of the stylet is placed in proximity to the distal end of the light wand in a first mode of operation and for enabling retracting or removing the stylet from the light-wand in a second mode of operation while the light-wand coupler and the connecting element remain coupled to the first holding structure and the second holding structure, respectively.

3. The intubation device according to claim 1 wherein a proximal end portion of the stylet is substantially stiff.

4. The intubation device according to claim 1 wherein the stylet is coated with a low friction coating.

5. The intubation device according to claim 1 wherein the flexible light-wand comprises a flexible sheath enclosing the light emitting means and the stylet.

6. The intubation device according to claim 1 comprising a release mechanism for disconnecting the tracheal tube port from the tracheal tube.

7. The intubation device according to claim 6 wherein the release mechanism comprises two rhombus shaped compression structures placed on opposite sides of the coupling conduit and fixedly mounted at a bottom portion thereof, each compression structure having a locking arm for retaining the tracheal tube connected to the tracheal tube port and for releasing the tracheal tube when a compressing force is applied to the compression structures.

8. An intubation device for placing a tracheal tube into a patient's trachea comprising:
    a flexible light-wand having light emitting means placed in a distal end portion thereof and a light-wand coupler at a proximal end thereof, a distal portion of the flexible light-wand being adapted for placement inside the tracheal tube with the distal end portion thereof being in proximity to a distal end of the tracheal tube;
    a coupling conduit, the coupling conduit having:
        a connecting element; and
        a tracheal tube port placed at a distal end thereof, the tracheal tube port for being connected to the tracheal tube; and
    a support structure having a first holding structure at a first end portion thereof and a second holding structure at a second opposite end portion thereof, the first holding structure being adapted for being removable coupled with the light-wand coupler, the second holding structure adapted for being removable coupled with the connecting element, the support structure extending continuously between the first holding structure and the second holding structure, wherein the support structure, the first holding structure and the second holding structure are adapted such that the support structure is entirely positioned at a predetermined distance to one side of the light-wand, the coupling conduit, and the tracheal tube wherein the second holding structure comprises a plurality of interacting elements, each interacting element for being removable coupled with the connecting element, each interacting element being placed at a predetermined location spaced apart from the location of each adjacent interacting element along a direction parallel to a longitudinal axis through the light-wand, the coupling conduit, and the tracheal tube, each location being associated with a predetermined distance between the coupling conduit and the proximal end of the flexible light-wand corresponding to a length of a tracheal tube of a plurality of tracheal tubes having different lengths such that in operation the distal end portion of the light-wand having a same length is in proximity to the distal end of each tracheal tube of the plurality of tracheal tubes.

9. The intubation device according to claim 8 wherein the flexible light-wand has sufficient flexibility for use in nasotracheal intubation.

10. The intubation device according to claim 8 wherein the first holding structure and the second holding structure have a predetermined distance therebetween such that in operation the distal end portion of the light-wand is in proximity to the distal end of the tracheal tube.

11. The intubation device according to claim 8 wherein the coupling conduit comprises a ventilating port for being connected to a ventilatory source and a monitoring port for being connected to a respiratory gas monitor and wherein the ventilating port and the respiratory gas monitor are placed on the coupling conduit substantially opposite the support structure.

12. The intubation device according to claim 8 wherein the support structure is adapted for accommodating therein a power source for powering the light emitting means.

13. An intubation device for placing a tracheal tube into a patient's trachea comprising:
    a flexible light-wand having light emitting means placed in a distal end portion thereof and a light-wand coupler at a proximal end thereof, a distal portion of the flexible light-wand being adapted for placement inside the tracheal tube with the distal end portion thereof being in proximity to a distal end of the tracheal tube;
    a coupling conduit, the coupling conduit having a connecting element and a tracheal tube port placed at a distal end thereof, the tracheal tube port for being connected to the tracheal tube; and,
    a support structure having a first holding structure at a first end portion thereof and a second holding structure at a second opposite end portion thereof, the support structure extending continuously between the first holding structure and the second holding structure, the first holding structure having a coupling element for being removable mated with the light-wand coupler, the second holding structure having an interacting element for being removable mated with the connecting element, the coupling element, the light-wand coupler, the interacting element, and the connecting element being adapted for securely holding each of the light-wand and the coupling conduit in a single predetermined location along a longitudinal axis through the light-wand, the coupling conduit, and the tracheal tube, the coupling element and the interacting element having a predetermined distance therebetween such that in operation the distal end portion of the light-wand is in proximity to the distal end of the tracheal tube wherein the second holding structure comprises a plurality of interacting elements, each interacting element being placed at a predetermined location spaced apart from the location of each adjacent interacting element along a direction parallel to the longitudinal axis, each location being associated with a predetermined distance between the coupling conduit and the proximal end of the flexible light-wand corresponding to a length of a tracheal tube of a plurality of tracheal tubes having different lengths such that in operation the distal end portion of the light-wand having a same length is in proximity to the distal end of each tracheal tube of the plurality of tracheal tubes.

14. The intubation device according to claim 13 wherein the coupling element, the light-wand coupler, the interacting element, and the connecting element comprise respective dove-tail shapes.

* * * * *